(12) United States Patent
Zhang

(10) Patent No.: US 11,116,909 B2
(45) Date of Patent: Sep. 14, 2021

(54) ELECTRICALLY POWERED NEEDLELESS INJECTOR

(71) Applicant: BEIJING QS MEDICAL TECHNOLOGY CO., LTD., Beijing (CN)

(72) Inventor: Ming Zhang, Beijing (CN)

(73) Assignee: BEIJING QS MEDICAL TECHNOLOGY CO., LTD., Beijing (CN)

( * ) Notice: Subject to any disclaimer, the term of this patent is extended or adjusted under 35 U.S.C. 154(b) by 302 days.

(21) Appl. No.: 15/506,509

(22) PCT Filed: Jul. 22, 2015

(86) PCT No.: PCT/CN2015/084819
§ 371 (c)(1),
(2) Date: Feb. 24, 2017

(87) PCT Pub. No.: WO2016/029758
PCT Pub. Date: Mar. 3, 2016

(65) Prior Publication Data
US 2017/0368261 A1    Dec. 28, 2017

(30) Foreign Application Priority Data

Aug. 27, 2014 (CN) .......................... 201420488275.X

(51) Int. Cl.
*A61M 5/30* (2006.01)
*A61M 5/315* (2006.01)

(52) U.S. Cl.
CPC ............. *A61M 5/30* (2013.01); *A61M 5/3007* (2013.01); *A61M 5/31501* (2013.01);
(Continued)

(58) Field of Classification Search
CPC ................ A61M 5/20; A61M 5/31501; A61M 5/31578; A61M 5/30; A61M 5/31571;
(Continued)

(56) References Cited

U.S. PATENT DOCUMENTS 4,435,173 A * 3/1984 Siposs ................. A61M 5/1456
128/DIG. 1
4,617,016 A * 10/1986 Blomberg ............... A61M 5/20
128/DIG. 1
(Continued)

FOREIGN PATENT DOCUMENTS

CN    201 524 322 U    7/2010
CN     201744024 U    2/2011
(Continued)

OTHER PUBLICATIONS

European Search Report, Extended, and Written Opinion dated Jan. 15, 2018 for Application No. EP 15835157.7, 6 pgs.
(Continued)

*Primary Examiner* — Nilay J Shah
(74) *Attorney, Agent, or Firm* — Frost Brown Todd LLC

(57) ABSTRACT

The present utility model provides an electrically powered needle-free injector (100), comprising: a needle-free injector body (120); and a needle-free injection end (130) extending distally from the needle-free injector body (120) for medicine administration, the needle-free injector body (120) comprises: a housing (3), an inside of which is divided into a pressurized injection chamber (123) and a motor chamber (124); a pressurized injection assembly (170) disposed within the pressurized injection chamber (123); a needle-free injector locking mechanism (180) at least partially disposed within the pressurized injection chamber; and a motor assembly (190) disposed within the motor chamber (124). The present utility model has a beneficial effect that it may provide a power source for the needle-free injector to
(Continued)

electrically take medicine and inject by a built-in motor; it works reliably, is used conveniently, and has a small size.

20 Claims, 3 Drawing Sheets

(52) U.S. Cl.
CPC .................. *A61M 5/31578* (2013.01); *A61M 2005/31588* (2013.01); *A61M 2205/10* (2013.01)

(58) Field of Classification Search
CPC ........... A61M 2005/31588; A61M 2005/3114; A61M 5/3204; A61M 5/3007; A61M 2005/202; A61M 5/3146
See application file for complete search history.

(56) References Cited

U.S. PATENT DOCUMENTS

| | | | |
|---|---|---|---|
| 4,959,056 A | 9/1990 | Dombrowski et al. | |
| 5,026,343 A | 6/1991 | Holzer | |
| 5,599,302 A * | 2/1997 | Lilley | A61M 5/30 604/135 |
| 5,647,851 A | 7/1997 | Pokras | |
| 6,003,736 A | 12/1999 | Ljunggren | |
| 7,235,063 B2 | 6/2007 | D'Antonio et al. | |
| 2002/0055707 A1* | 5/2002 | Slate | A61M 5/30 604/72 |
| 2008/0319383 A1* | 12/2008 | Byland | A61M 5/1782 604/67 |
| 2012/0302947 A1* | 11/2012 | Canton | A61M 5/30 604/68 |

FOREIGN PATENT DOCUMENTS

| | | |
|---|---|---|
| CN | 103495241 A | 1/2014 |
| CN | 103816587 A | 5/2014 |
| CN | 104147666 A | 11/2014 |
| CN | 204033941 U | 12/2014 |
| JP | 2008-521522 A | 6/2008 |
| JP | 2012-532722 A | 12/2012 |
| WO | WO 2016/029758 A1 | 3/2016 |

OTHER PUBLICATIONS

International Search Report dated Oct. 23, 2015 for Application No. PCT/CN2015/084819, 8 pgs.
International Written Opinion dated Oct. 23, 2015 for Application No. PCT/CN2015/084819, 5 pgs.
Japanese Office Action, Notice of Reasons for Refusal, dated Dec. 11, 2018 for Application No. JP 2017-530382, 2 pgs.
Japanese Office Action, Decision to Grant a Patent, dated Mar. 19, 2019 for Application No. JP 2017-530382, 2 pgs.
Japanese Office Action, Notice of Reasons for Refusal, and Search Report by Registered Search Organization, dated Mar. 10, 2020, for Application No. JP 2019-073525, 58 pgs.
Japanese Office Action, Final Notification of Reasons for Refusal, dated Jul. 14, 2020 for Application No. JP 2019-073525, 4 pgs.

\* cited by examiner

ELECTRICALLY POWERED NEEDLELESS INJECTOR

FIELD OF THE INVENTION

The present utility model relates to the technical field of medicine and medical equipment, and more particularly, to an electrically-powered needle-free injector.

BACKGROUND OF THE INVENTION

With the development of the pharmaceutical industry, a number of biological preparations have emerged, characterized by a small injection amount and repeated injection. A needle injector causes needle phobia and acupuncture pain, which, however, can be effectively avoided by a needle-free injector.

Current commercially available needle-free injectors usually pressurize liquid medicine through an external power source, such that the liquid medicine penetrates the skin through very fine micropores at high pressure and high speed into the body. In other words, the liquid medicine can straightly penetrate the human or animal skin into the body without a needle. Meanwhile, the needle-free injector may also make the injected medicine more disperse, which facilitates absorption of the medicine and reduces invasion of subcutaneous tissues, thereby avoiding formation of induration.

However, since needle-free injectors have not been around for quite a while, they still have many drawbacks. For example, the current civilian needle-free injectors are basically pressurized manually, which are very inconvenient for users. The electric needle-free injectors used in large and medium-sized hospitals have a longer length, and thus a larger size, which are also very inconvenient to be operated.

In actual production and life, there is an urgent need for a needle-free injector hick can be easily operated and has a simple structure.

SUMMARY OF THE INVENTION

An objective of the utility model is to provide an electrically-powered needle-free injector which may take medicine and inject electrically through a built-in motor, works reliably, is operated conveniently, and has a small size.

According to the utility model, there is provided an electrically-powered needle-free injector, comprising: a needle-free injector body; and a needle-free injection end extending distally from the needle-free injector body for medicine administration. The needle-free injector body comprises: a housing, an inside of which is divided into a pressurized injection chamber and a motor chamber; a pressurized injection assembly disposed within the pressurized injection chamber; a needle-free injector locking mechanism at least partially disposed within the pressurized injection chamber; and a motor assembly disposed within the motor chamber.

According to a preferred embodiment, a longitudinal axis of the pressurized injection assembly is parallel to a longitudinal axis of the motor assembly.

According to a preferred embodiment, the pressurized injection assembly comprises: a push rod, a pressure spring sleeved on the push rod, and a compression body at least partially encircling the push rod and the pressure spring.

According to a preferred embodiment, a push rod boss is provided at a distal side of the push rod, and a step shoulder is provided inside of the compression body, a distal end of the pressure spring abuts against the push rod boss and a proximal end of the pressure spring abuts against the step shoulder, such that when the compression body is driven by the motor assembly, the pressure spring can be pressurized.

According to a preferred embodiment, the needle-free injector locking mechanism can lock the compression body and the push rod together via a locking ball passing through a wall of the compression body and entering into a groove at a proximal end of the push rod, thereby locking the pressure spring in a pressurized state.

According to a preferred embodiment, the needle-free injector locking mechanism comprises a hollow button, an inner end of the button having a flat step and a button groove disposed proximal to the flat step; in a locked state, the flat step abuts against the locking ball that passes through the wall of the compression body and enters into the groove at the proximal end of the push rod to prevent detachment of the locking ball; to unlock for injection, the button is depressed to move the flat step to a distal side, and the locking ball is pushed to enter into the button groove to allow unlocking of the push rod from the compression body.

According to a preferred embodiment, the compression body comprises a compression body main body of a substantially sleeve-shaped structure and a force-transmitting portion extending upward from the compression body main body, the force-transmitting portion being formed with a central hole for receiving the motor assembly.

According to a preferred embodiment, the compression body main body comprises an inner wall thickened portion to form: (a) the step shoulder for abutting against the proximal end of the pressure spring; and (b) a deep groove longitudinally extending from the proximal end of the compression body main body, for receiving a portion of the needle-free injector locking mechanism.

[001.] According to a preferred embodiment, a partitioning wall extending proximally from an inner side of a distal wall of the housing and an upper-side wall of the compression body main body together divide the inside of the housing into the pressurized injection chamber and the motor chamber.

According to a preferred embodiment, the partitioning wall supports, at above, a motor of the motor assembly.

According to a preferred embodiment, the motor assembly comprises: a motor, a motor shaft projecting from the motor, and a screw rod connected to the motor shaft, the screw rod extending along an axis of the motor assembly and passing through the central hole of the force-transmitting portion.

According to a preferred embodiment, the needle-free injector locking mechanism comprises: a hollow button inserted into the deep groove at the proximal end of the compression body main body, an inner end of the button having a flat step and a button groove disposed proximal to the flat step; a lock column whose proximal end is disposed inside the button and contacts with an inner wall of the button; a button spring disposed inside the button and positioned proximal to the lock column; a small hole in a wall of the compression body; a locking ball; and a groove of the push rod.

In the present utility model, a longitudinal axis of the pressurized injection assembly is parallel to a longitudinal axis of the motor assembly, such that compared with a co-axial structure, a length of the needle-free injector may be shortened. The utility model has a built-in motor and may accurately control start, stop, clockwise rotation and counterclockwise rotation of the motor.

In the present utility model, a partitioning wall extending proximally from an inner side of a distal wall of the housing and an upper-side wall of the compression body main body together divide the inside of the housing into the pressurized injection chamber and the motor chamber, which makes the structure more compact and simpler.

The present utility model has a beneficial effect that it may provide a power source for the needle-free injector to electrically take medicine and inject by a built-in motor; it works reliably, is used conveniently, and has a small size.

BRIEF DESCRIPTION OF THE ACCOMPANYING DRAWINGS

DETAILED DESCRIPTION OF THE PREFERRED EMBODIMENTS

Figure 1:
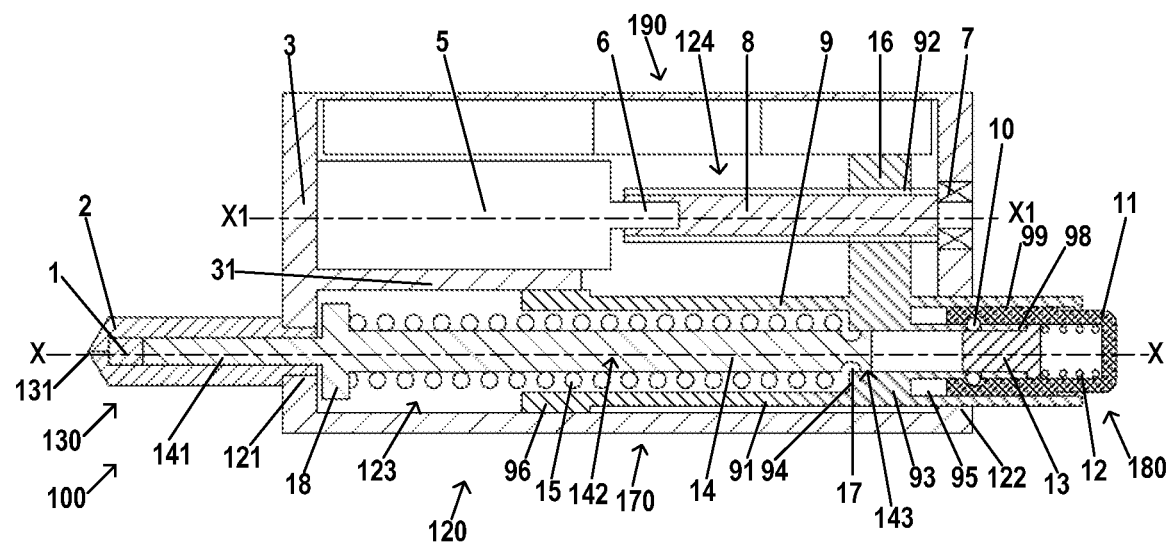
FIG. 1 is a longitudinal sectional view of a needle-free injector according to preferred embodiment of the present utility model, where the needle-free injector is in a released state.

According to spirit of the present utility model, there exist a plurality of embodiments to achieve objectives of the present utility model. Hereinafter, a structure, configuration, and working principle of the needle-free injector of the present utility model will be explained according to preferred embodiments shown in the drawings. With reference to the preferred embodiments, those skilled in the art may envisage other embodiments that can achieve the objectives of the present utility model.

In the context of the present disclosure, the term "distal side" refers to a side of the needle-free injector during use proximal to a patient's skin; the term "proximal side" refers to a side of the needle-free injector during use distal from a patient's skin; the terms "above," "below," "left," and "right" are relative to the figure plane shown in the drawings, the terms "longitudinal" and "radial" are relative to the longitudinal axis of the needle-free injector. Besides, like parts are indicated by the same reference numerals.

Figure 2:
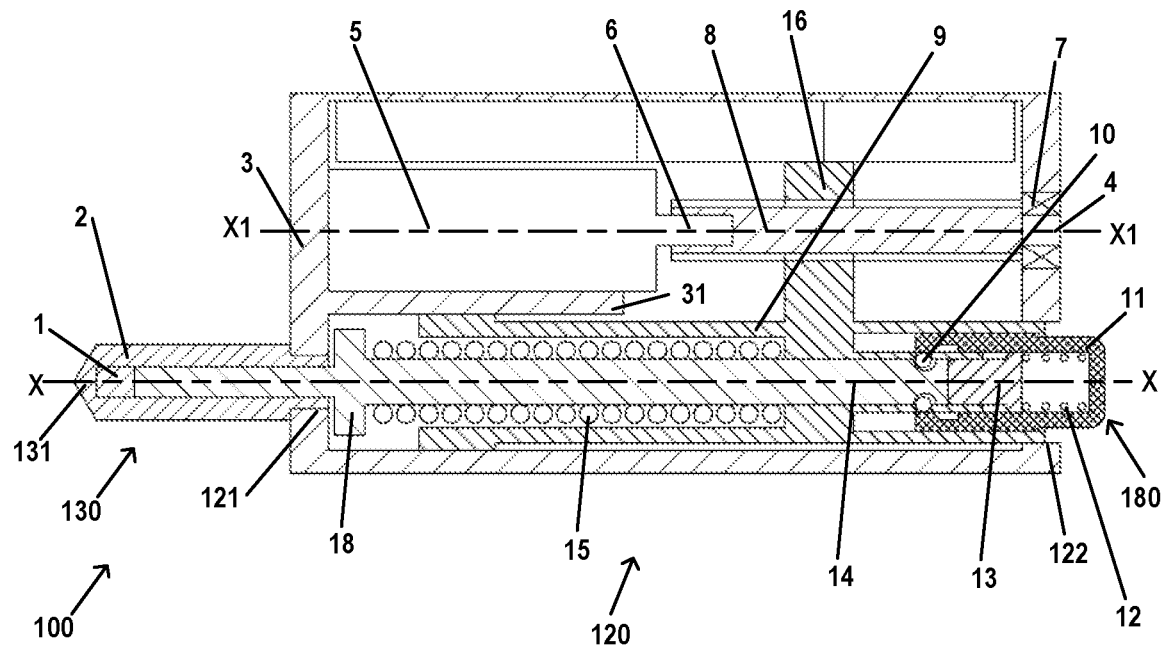
FIG. 2 is a schematic diagram of the needle-free injector of FIG. 1 in a pressurized state.
Figure 3:
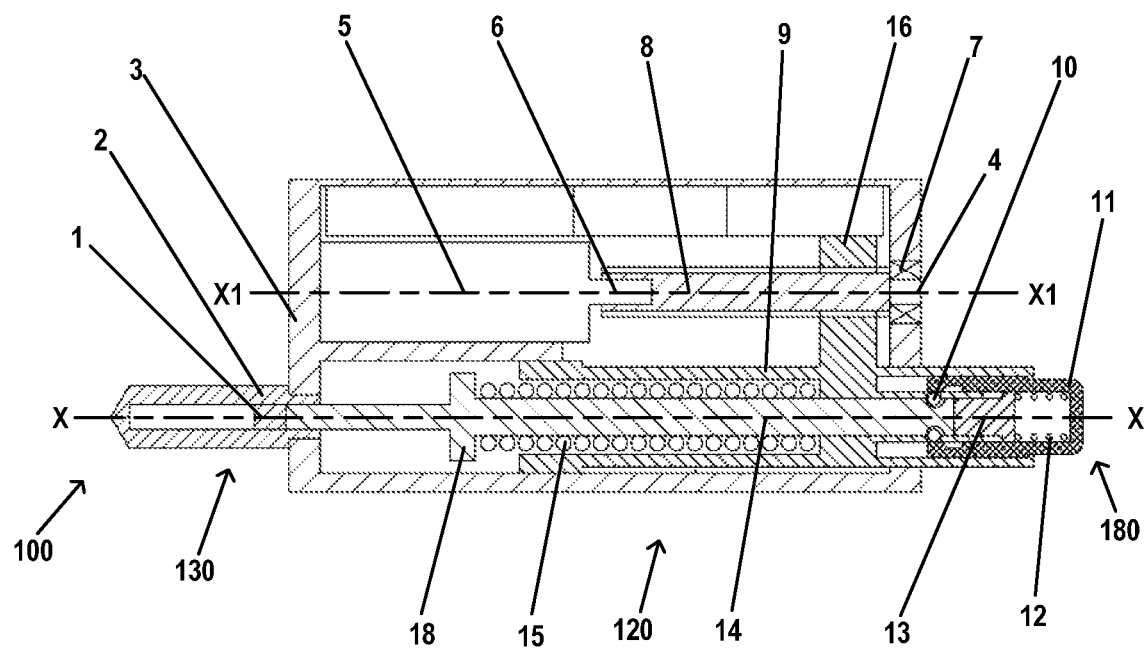
FIG. 3 is a schematic diagram of the needle-free injector of FIG. 1 in a state of taking medicine and adjusting dosage.
Figure 4:
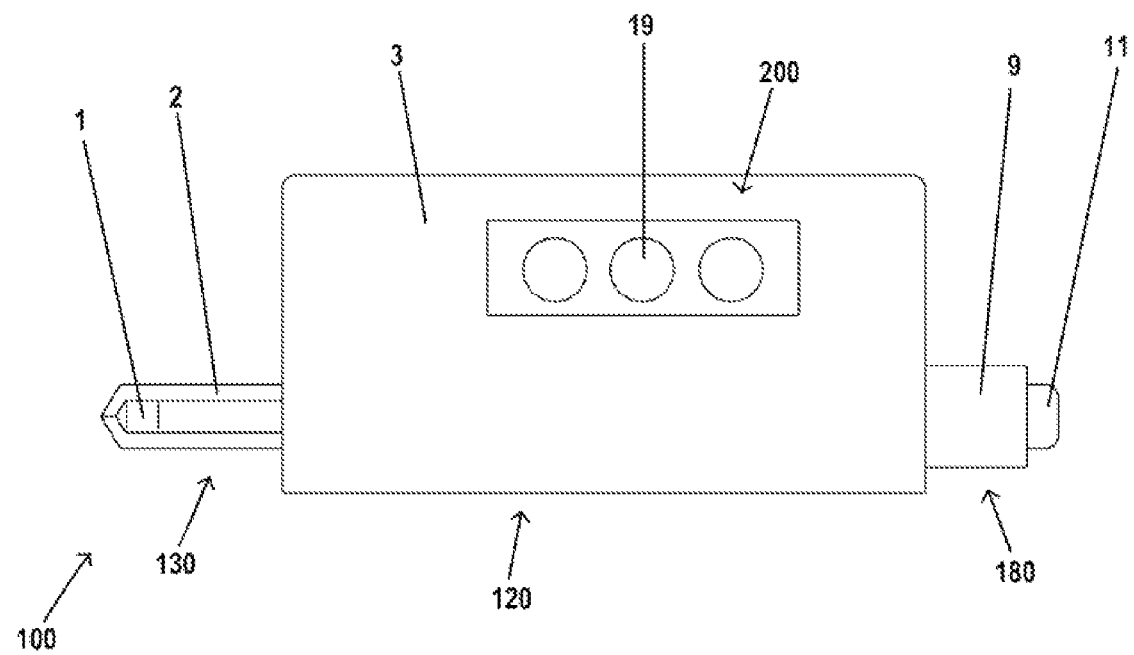
FIG. 4 is a schematic diagram of an appearance of a needle-free injector according to a preferred embodiment of the present utility model.

FIG. 4 is a schematic diagram of an appearance of a needle-free injector 100 according to a preferred embodiment of the present utility model. The needle-free injector 100 according to the present utility model comprises: a needle-free injector body 120; and a needle-free injection end 130 extending distally from the needle-free injector body 120 for medicine administration. Referring to FIGS. 1-3, the needle-free injector body 120 comprises: a housing 3, an inside of which is divided into a pressurized injection chamber 123 and a motor chamber 124; a pressurized injection assembly 170 disposed within the pressurized injection chamber 123; a needle-free injector locking mechanism 180 at least partially disposed within the pressurized injection chamber 123; and a motor assembly 190 disposed within the motor chamber 124.

According to a preferred embodiment of the present utility model, a distal end lower side of the housing 3 is provided with a first hole 121 available for the needle-free injection end 130 to extend distally from the needle-free injector body 120 (see FIGS. 1-3), and a proximal end lower side of the housing 3 is provided with a second hole 122 available for the needle-free injector locking mechanism 180 to extend proximally out of the housing 3 (see FIGS. 1-3). In addition, an exterior side of the housing 3 is also provided with control means 200. In a preferred embodiment, the control means 200 may comprise at least one control button, e.g., a switching key 19, etc., so as to separately or collectively control release, pressurization, and taking-medicine of the needle-free injector 100.

FIG. 1 is a longitudinal sectional view of the needle-free injector 100 according to a preferred embodiment of the present utility model, where the needle-free injector 100 is in a released state. As shown in FIG. 1, an inside of the housing 3 of the needle-free injector 100 is divided into a pressurized injection chamber 123 and a motor chamber 124. The housing 3 may be split or integral. The pressurized injection assembly 170 has a pressurized injection assembly longitudinal axis X-X through centers of the first hole 121 and second hole 122, and a motor assembly longitudinal axis X1-X1 of the motor assembly 190 driving the needle-free injector 100. As illustrated in FIG. 1, the pressurized injection assembly longitudinal axis X-X and the motor assembly longitudinal axis X1-X1 are parallel to each other.

As shown in the drawings, in general, the electrically-powered needle-free injector 100 according to the present utility model comprises: a piston 1, a medicine tube wall 2, the housing 3, a motor 5, a screw rod 8, a compression body 9, a steel ball 10, a button 11, a button spring 12, a lock column 13, a push rod 14, and a pressure spring 15, the compression body being of a tubular structure, a screw nut 16 extending perpendicularly at an outside wall of the compression body 9, the screw rod 8 being socketed on the screw nut, one end of the screw rod being connected to a motor shaft 6; the other end of the screw rod being connected to one end of the housing 3; an axis of the push rod 14 (i.e., the pressurized injection assembly longitudinal axis X-X) is parallel to an axis of the motor shaft 6 (i.e., the motor assembly longitudinal axis X1-X1).

Specifically, as shown in FIG. 1, the needle-free injection end 130 comprises a medicine tube wall 2 extending distally from the first hole 121 of the housing 3 and the piston 1 disposed within the medicine tube wall 2. Particularly, the medicine tube wall 2 is of a substantially cylindrical shape and has a substantially closed conical distal end and an open diameter-diminished proximal end. The conical distal end has a micropore 131 through a conical apex, for squirting medicine liquid during use. The diameter-diminished portion of the diameter-diminished proximal end may be just received within the first hole 121, and a step shoulder formed by the diminished diameter abuts against an external side of a distal wall of the housing 3. Of course, those skilled in the art may understand that a connection between the needle-free injection end 130 and the housing 3 is not limited thereto; besides, the diameter-diminished portion and the first hole 121 may be joined in any known manner, including, but not limited to, adhesion, screwed connection, etc.

As mentioned above, the needle-free injector 100 also comprises: the pressurized injection assembly 170 disposed within the pressurized injection chamber 123; the needle-free injector locking mechanism 180 at least partially disposed within the pressurized injection chamber 123; and the motor assembly 190 disposed within the motor chamber 124. Particularly, the pressurized injection assembly 170 comprises: the push rod 14, the pressure spring 15 sleeved on the push rod 14, and the compression body 9 at least partially encircling the push rod 14 and the pressure spring 15. Particularly, the pressure spring 15 can be pressurized, while the needle-free injector locking mechanism 180 can lock it in a pressurized state and unlock it in the need of injection. Specifically, the push rod 14 extends along the pressurized injection assembly longitudinal axis X-X and has a push distal end 141 that may extend into the medicine tube wall 2 and a proximal end portion 142. A push rod boss 18 is formed between the push distal end 141 and the proximal portion 142; when the push rod 14 completes medicine injection, the push rod boss 18 may press against a distal wall inner side of the housing 3. A proximal end 143 of the push rod 14 is provided with a groove 17 that is arranged peripherally around the push rod 14. The pressure spring 15 is sleeved on the proximal portion 142 of the push rod 14, while a distal end of the pressure spring abuts against the push rod boss 18.

Besides, still referring to FIGS. 1-3, the compression body 9 comprises a compression body main body 91 of a substantially sleeve-shaped structure and a force-transmitting portion extending upward from the compression body main body 91, i.e., a screw nut 16. The force-transmitting portion is substantially positioned at a proximal portion of the sleeve-shaped structure of the compression body main body 91, and an inner wall thickened portion 93 is formed because an inner wall of the proximal portion of the sleeve-shaped structure corresponding to the force-transmitting portion is inwardly thickened; a step shoulder 94 is formed at an intersection between the inner wall thickened portion 93 and the remaining portion of the sleeve-shaped structure. The inner wall thickened portion 93 has an inner diameter substantially identical to an outer diameter of the push rod 14. A proximal portion of the inner wall thickened portion 93 is formed with a deep groove 95 extending longitudinally from the proximal end for receiving the needle-free injector locking mechanism 180. Moreover, the proximal portion of the compression body main body 91 may extend out from the second hole 122. Besides, the force-transmitting portion is formed with a central hole 92 through which the screw rod 8 passes. Preferably, a flange 96 is provided at an outer side of the distal end of the compression body main body 91. As shown in FIGS. 1-3 and 5, the deep groove 95 causes that the proximal portion of the compression body main body 91 has a first inner side wall 98 and a second outer side wall 99, and small holes 101 are formed at corresponding portions of the first inner side wall 98 (e.g., the upper and lower positions shown in the figure).

After the assembly, the proximal portion of the compression body main body 91 extends out from the second hole 122; the flange 96 at its lower side is supported on a lower wall of the housing 3 and at its upper side contacts with a segment of a partitioning wall 31 extending proximally from an inner side of the distal wall of the housing 3; the push rod 14 and the pressure spring 15 sleeved on the push rod 14 are disposed within the compression body main body 91, and the other end of the pressure spring 15 abuts against the step shoulder 94. In this way, the partitioning wall 31 and the wall of the compression body main body 91 form the pressurized injection chamber 124.

As illustrated in FIG. 1, the partitioning wall 31 supports, at above, the motor 5, and the screw rod 8 connected to the motor shaft 6 of the motor 5 extends along the motor assembly axis X1-X1 and passes through the hole 92 of the power-transmitting portion, i.e., the screw nut 16. A rotary shaft 4 at the other end of the screw rod is rotatably connected to the housing 3 via a bearing 7.

In other words, the piston 1 positioned within the medicine tube wall 2 plays a role of sealing the medicine during taking medicine and injection. Connected to the piston 1 is the push rod 14 outside of which is sleeved the pressure spring 15; a groove 17 disposed at a rear end side wall of the push rod 14 may receive the steel ball 10 in a locked state (which will be discussed infra). A front end of the pressure spring 15 contacts the push rod boss 18 of the push rod 14, and a rear end of the pressure spring 15 contacts with the compression body 9 inner step. The compression body 9 may be axially displaced to compress and move the pressure spring 15. The screw nut 16 connected to the compression body 9 has an inner screw that is screwed with the screw rod 8. Rotation of the screw rod 8 will lead to axial displacement of the screw nut 16. The screw rod 8 is connected to the motor 5, such that when the motor 5 rotates, the screw rod 8 will rotate together.

Figure 5:
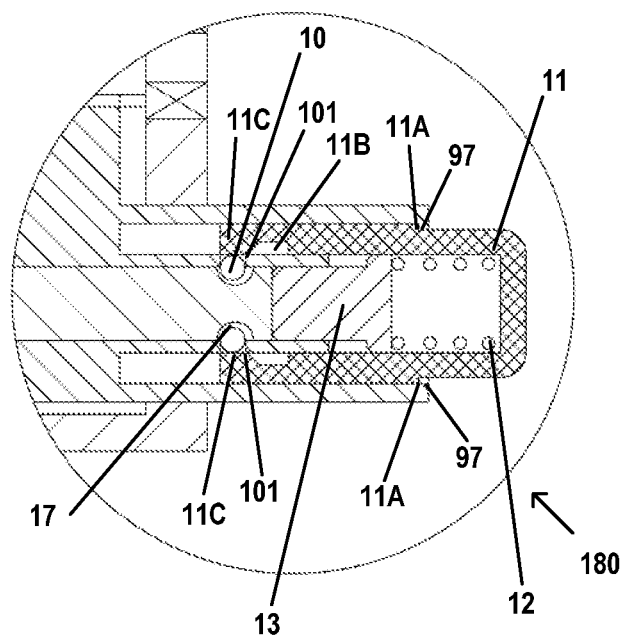
FIG. 5 is a locally enlarged view of a rear part of FIG. 3.

FIG. 5 is a locally enlarged view of a rear part of FIG. 3, emphatically showing the needle-free injector locking mechanism 180. The needle-free injector locking mechanism 180 locks the push rod 14 with the compression body 9 by virtue of a locking ball engaged with holes or grooves in walls of different members, e.g., steel ball 10, such that the compression spring 15 is held in a pressurized state.

More specifically, as shown in FIG. 5, the needle-free injector locking mechanism 180 comprises: steel balls 10 that may freely pass through small holes 101 in the first inner side wall 98 of the compression body main body 91, the groove 17 of the push rod, a groove 11B and a locking flat step 11C formed in the side wall of the button 11.

Referring to FIG. 5, the hollow button 11 has a longitudinal cross section of a substantially U-shape and a step shoulder 11A formed on its outside wall, such that after the button is inserted into the deep groove 95 of the proximal end of the compression body main body 91 and moved to the most proximal side position, the step shoulder 11A abuts against an inner flange 97 formed by an outer wall of the proximal end of the compression body main body 91, thereby preventing the button 11 from being disengaged from the needle-free injector. Besides, the groove 11B is formed at an inner wall distal portion of the button 11. A longitudinal cross-section of the lock column 13 is of a substantially T shape, the maximum diameter of the proximal end of the T-shape is consistent with an inner diameter of the button 11. After being mounted, the proximal end of the lock column 13 is disposed within the button 11 and contacts with the inner wall of the button 11; a button spring 12 is disposed within the button 11 and positioned proximal to the lock column 13, one end of the button spring abutting against the proximal end of the lock column 13, the other end abutting against the proximal wall of the button 11; a smaller-diameter cylindrical portion of the lock column 13 extends inside the proximal side portion of the sleeve-shaped structure of the compression body main body 91.

When the injector needs to work, by touching a switching key 19 of control means 200, the motor 5 will rotate to cause rotation of the screw rod 8, while rotation of the screw rod 8 will thread drive the compression body 9 to move to the left. Because the distal end of the pressure spring 15 abuts against the push boss 18 and the proximal end of the pressure spring 15 abuts against the step shoulder 94 of the compression body 9, as the compression body 9 moves to the left, the pressure spring 15 will be pressurized. Meanwhile, a right end of the push rod 14 approaches to the lock column 13 and pushes the lock column 13 to compress the button spring 12. When the compression body moves to a certain position, the steel ball 10 may enter into the groove 17 at the right end of the push rod 14, and the button 11 will be ejected out under the action of the button spring 12. The flat step at the end portion of the button 11 presses the steel hall 10 into the groove at the right end of the push rod 14, thereby locking the push rod 14 with the compression body 9; in this way, the pressure spring 15 is locked in the pressurized state, as shown in FIG. 2.

Afterwards, the injector enters into the process of taking medicine and regulating dosage (FIG. 3 shows a state of taking medicine and regulating dosage). When the motor 5 rotates reversely, the compression body 9 will move to the right side to drive the push rod (at this time, the push rod 14 is locked together with the compression body 9), the piston 1, the compression spring 15, and the lock column 13 to move together to the right side. During the movement process, a negative pressure will be formed inside the medicine tube wall 2, and then the medicine will enter into the medicine tube wall 2 through the small hole at the front end of the medicine tube wall 2. Meanwhile, an interstice is formed between the step shoulder at the left of the push rod 14 and the housing 3. The size of the interstice is decided by the injection dosage.

When injecting the medicine, the button 11 is pressed down to be moved to the left; the steel ball, pushed by the push rod 14, enters into the groove of the button 11. The push rod 14 is not bound by steel ball, and the push rod 14 and the compression body 9 will not be locked any longer; the pressure spring 15 in the pressurized state will act; the push rod 14, under the action of the pressure spring 15, moves promptly to the left. The elasticity of the pressure spring 15 acts on the medicine in the medicine tube wall 2 under the action of the push rod 14 and the piston 1, such that the medicine is rapidly squirted out and injected into the body. Then, one working process is completed, and the needle-free injector returns to the state of FIG. 1.

What have been mentioned above are preferred embodiments of the present utility model and the technical principle as applied. To those skilled in the art, without departing from the spirit and scope of the present utility model, any obvious changes such as equivalent transformations and simple substitutions based on the technical solutions of the present utility model fall within the protection scope of the utility model.

The invention claimed is:

1. An integrated electrically-powered needle-free injector (100), comprising:
a needle-free injector body (120); and
a needle-free injection end (130) extending distally out from the needle-free injector body (120) for administration of a medicine, the needle-free injector body (120) being inseparable from the needle-free injection end (130) during the administration of the medicine;
the needle-free injector body (120) comprises:
a housing (3), an inside of which is divided into a pressurized injection chamber (123) and a motor chamber (124);
a pressurized injection assembly (170) disposed within the pressurized injection chamber (123);
a needle-free injector locking mechanism (180) at least partially disposed within the pressurized injection chamber (123); and
a motor assembly (190) disposed within the motor chamber (124);
wherein the pressurized injection assembly (170) is configured to only translate, without any rotation, with respect to the housing (3) when driven by the motor assembly (190).

2. The integrated needle-free injector (100) according to claim 1, characterized in that a longitudinal axis (X-X) of the pressurized injection assembly (170) is parallel to a longitudinal axis (X1-X1) of the motor assembly (190).

3. The integrated needle-free injector (100) according to claim 2, characterized in that the pressurized injection assembly (170) comprises: a push rod (14), a pressure spring (15) sleeved on the push rod (14), and a compression body (9) at least partially encircling the push rod (14) and the pressure spring (15).

4. The integrated needle-free injector (100) according to claim 1, characterized in that the pressurized injection assembly (170) comprises: a push rod (14), a pressure spring (15) sleeved on the push rod (14), and a compression body (9) at least partially encircling the push rod (14) and the pressure spring (15).

5. The integrated needle-free injector (100) according to claim 4, characterized in that a push rod boss (18) is provided at a distal side of the push rod (14), and a step shoulder (94) is provided inside of the compression body (9), a distal end of the pressure spring (15) abuts against the push rod boss (18) and a proximal end of the pressure spring (15) abuts against the step shoulder (94), such that when the compression body (9) is driven by the motor assembly (190), the pressure spring (15) can be pressurized.

6. The integrated needle-free injector (100) according to claim 5, characterized in that the needle-free injector locking mechanism (180) can lock the compression body (9) and the push rod (14) together via a locking ball (10) passing through a wall of the compression body (9) and entering into a groove (17) at a proximal end of the push rod (14), thereby locking the pressure spring (15) in a pressurized state.

7. The integrated needle-free injector (100) according to claim 6, characterized in that the needle-free injector locking mechanism (180) comprises a hollow button (11), an inner end of the button (11) having a flat step (11C) and a button groove (11B) disposed proximal to the flat step; in a locked state, the flat step (11C) abuts against the locking ball (10) that passes through the wall of the compression body (9) and enters into the groove (17) at the proximal end of the push rod (14) to prevent detachment of the locking ball; to unlock for injection, the button (11) is depressed to move the flat step (11C) to a distal side, and the locking ball (10) is pushed to enter into the button groove (11B) to allow unlocking of the push rod (14) from the compression body (9).

8. The integrated needle-free injector (100) according to claim 5, characterized in that the compression body (9) comprises a compression body main body (91) of a sleeve-shaped structure and a force-transmitting portion (16) extending upward from the compression body main body (91), the force-transmitting portion (16) being formed with a central hole (92) for receiving the motor assembly (190).

9. The integrated needle-free injector (100) according to claim 8, characterized in that the compression body main body (91) comprises an inner wall thickened portion (93) to form: (a) the step shoulder (94) for abutting against the proximal end of the pressure spring (15); and (b) a deep groove (95) longitudinally extending from a proximal end of the compression body main body (91), for receiving a portion of the needle-free injector locking mechanism (180).

10. The integrated needle-free injector (100) according to claim 9, characterized in that the needle-free injector locking mechanism (180) comprises: a hollow button (11) inserted into the deep groove (95) at the proximal end of the compression body main body (91), an inner end of the button (11) having a flat step (11C) and a button groove (11B) disposed proximal to the flat step; a lock column (13)

whose proximal end is disposed inside the button (11) and contacts with an inner wall of the button (11); a button spring (12) disposed inside the button (11) and positioned proximal to the lock column (13); a small hole (101) in a wall of the compression body (9); a locking ball (10); and a groove (17) of the push rod (14).

11. The integrated needle-free injector (100) according to claim 8, characterized in that a partitioning wall (31) extending proximally from an inner side of a distal wall of the housing (3) and an upper-side wall of the compression body main body (91) divide the inside of the housing (3) into the pressurized injection chamber (123) and the motor chamber (124).

12. The integrated needle-free injector (100) according to claim 11, characterized in that the partitioning wall (31) supports, at above, a motor (5) of the motor assembly (190).

13. The integrated needle-free injector (100) according to claim 8, characterized in that the motor assembly (190) comprises: a motor (5), a motor shaft (6) projecting from the motor (5), and a screw rod (8) connected to the motor shaft (6), the screw rod (8) extending along a longitudinal axis (X1-X1) of the motor assembly and passing through the central hole (92) of the force-transmitting portion.

14. The integrated needle-free injector (100) according to claim 13, characterized in that the screw rod (8) is not coaxial with the pressure spring (15).

15. The integrated needle-free injector (100) according to claim 1, characterized in that the housing (3) of the needle-free injector body (120) is inseparable from the needle-free injection end (130) during the administration of the medicine using an adhesive.

16. The integrated needle-free injector (100) according to claim 1, characterized in that the housing (3) of the needle-free injector body (120) is inseparable from the needle-free injection end (130) during the administration of the medicine using a screwed connection.

17. An integrated electrically-powered needle-free injector (100), comprising:
a needle-free injector body (120); and
a needle-free injection end (130) extending distally out from the needle-free injector body (120) for administration of a medicine, the housing (3) of the needle-free injection end (130) being coupled with the needle-free injector body (120) during the administration of the medicine,
the needle-free injector body (120) comprises:
a housing (3), an inside of which is divided into a pressurized injection chamber (123) and a motor chamber (124);
a pressurized injection assembly (170) disposed within the pressurized injection chamber (123), the pressurized injection assembly (170) comprising a push-rod (14), the push-rod (14) comprising a push distal end (141) extending distally out of the needle-free injector body (120);
a needle-free injector locking mechanism (180) at least partially disposed within the pressurized injection chamber (123); and
a motor assembly (190) disposed within the motor chamber (124);
wherein the pressurized injection assembly (170) is configured to only translate, without any rotation, with respect to the housing (3) when driven by the motor assembly (190).

18. The integrated needle-free injector (100) according to claim 17, characterized in that the needle-free injection end (130) is coupled with the needle-free injector body (120) during the administration of the medicine using an open diameter-diminished proximal end that is received within a first hole (121), and a step shoulder formed by the open diameter-diminished proximal end that abuts against an external side of a distal wall of the housing (3).

19. An integrated electrically-powered needle-free injector (100), comprising:
a needle-free injector body (120); and
a needle-free injection end (130) extending distally out from the needle-free injector body (120) for administration of a medicine, the needle-free injection end (130) being coupled with the needle-free injector body (120) during the administration of the medicine;
the needle-free injector body (120) comprises:
a housing (3), an inside of which is divided into a pressurized injection chamber (123) and a motor chamber (124);
a pressurized injection assembly (170) disposed within the pressurized injection chamber (123);
a needle-free injector locking mechanism (180) at least partially disposed within the pressurized injection chamber (123), the needle-free injector locking mechanism (180) including a hollow button (11) and a button spring (12), the hollow button (11) circumferentially surrounding the button spring (12); and
a motor assembly (190) disposed within the motor chamber (124);
wherein the pressurized injection assembly (170) is configured to only translate, without any rotation, with respect to the housing (3) when driven by the motor assembly (190).

20. The integrated needle-free injector (100) according to claim 19, characterized in that the housing (3) of the needle-free injector body (120) is inseparable from the needle-free injection end (130) during the administration of the medicine using an adhesive or a screwed connection.

* * * * *